United States Patent [19]

Hsu et al.

[11] Patent Number: 5,883,134
[45] Date of Patent: Mar. 16, 1999

[54] BROAD-SPECTRUM ANTIMICROBIALLY ACTIVE COMPOUNDS

[75] Inventors: Adam Chi-Tung Hsu, Lansdale; Peter Osei-Gyimah, Horsham; Barry C. Lange, Lansdale; Rhoda W. Joseph, Buckingham, all of Pa.

[73] Assignee: Rohm and Haas Company, Philadelphia, Pa.

[21] Appl. No.: 701,145

[22] Filed: Aug. 21, 1996

Related U.S. Application Data

[60] Provisional application No. 60/003,143, Sep. 1, 1995.
[51] Int. Cl. $^6$ .................................................. A01N 41/10
[52] U.S. Cl. ........................... 514/708; 514/709; 514/710
[58] Field of Search .................................... 514/708, 709, 514/710

[56] References Cited

U.S. PATENT DOCUMENTS

| 3,242,041 | 3/1966 | Aichenegg et al. | 514/710 |
| 4,028,379 | 6/1977 | White | 260/309 |
| 4,451,660 | 5/1984 | Dolman et al. | 549/63 |

*Primary Examiner*—Allen J. Robinson
*Attorney, Agent, or Firm*—Julie J. L. Cheng; S. Matthew Cairns

[57] ABSTRACT

Disclosed is a method of controlling or inhibiting the growth of microorganisms comprising introducing in, at, or on a locus an antimicrobially effective amount of an antimicrobially active nitroethene compound.

5 Claims, No Drawings

BROAD-SPECTRUM ANTIMICROBIALLY ACTIVE COMPOUNDS

This is a nonprovisional application of prior pending provisional application Ser. No. 60/003,143, filed Sep. 1, 1995.

This invention relates to novel antimicrobially active compounds and their use in controlling or inhibiting the growth of microorganisms.

Antimicrobially active compounds are known to be used to control a broad spectrum of microorganisms in various applications. It is known that antimicrobially active compounds frequently are active against bacteria and not against fungi, or vice versa. Many antimicrobially active compounds are active against bacteria and fungi, but not against algae, or vice versa. This lack of broad spectrum activity frequently leads to a need to use a combination of antimicrobially active compounds to protect a locus.

A broad spectrum antimicrobially active compound is desired to provide protection of a locus with a single antimicrobially active compound.

It is an object of the present invention to provide a method of controlling or inhibiting the growth of microorganisms comprising introducing in, at, or on a locus an antimicrobially effective amount of an antimicrobially active compound. It is a further object of the present invention to provide antimicrobial agents which have fungicidal, bactericidal and/or algaecidal activity and function to kill or inhibit the growth of microbial organisms present in various loci.

These and other objects which will become apparent from the following disclosure are achieved by the present invention which in one aspect comprises a method of controlling or inhibiting the growth of microorganisms comprising introducing in, at, or on a locus an antimicrobially effective amount of an antimicrobially active compound of the formula

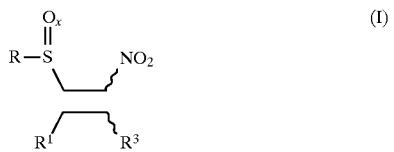

wherein $R^1$ is selected from $R^2SO_y$, H, and $(C_1-C_{18})$alkyl;

R and $R^2$ are independently selected from $(C_1-C_{18})$alkyl;

R and $R^2$ can be joined, together with the atoms to which they are attached, to form a 5-membered or 6-membered saturated or unsaturated ring, said ring optionally fused to a substituted or unsubstituted phenyl ring;

R and $R^1$ can be joined, together with the atoms to which they are attached, to form a 5-membered or 6-membered saturated or unsaturated ring;

$R^3$ is selected from H, and $(C_1-C_6)$alkyl;

$R^1$ and $R^3$ or R and $R^3$ can be joined, together with the atoms to which they are attached, to form a 5-membered or 6-membered unsaturated ring;

x=1 or 2; and y=0, 1, or 2.

This invention also relates to antimicrobially active compounds according to formula I provided that when R is methyl, x=1, and $R^3$=H, $R^1$ is not thiomethyl.

By substituted phenyl is meant a phenyl group having one or more of its hydrogens replaced with another substituent group. Examples of suitable substituent groups include $(C_1-C_3)$alkyl, $(C_1-C_3)$alkoxy, hydroxy, nitro, halo, cyano, and $(C_1-C_3)$alkylthio.

As used herein, "antimicrobially active compounds" include fungicides, bactericides and algaecides and antimicrobial activity is intended to include both the elimination of and inhibition or prevention of growth of microbial organisms such as fungi, bacteria, and algae.

U.S. Pat. No. 4,028,379 assigned to Smith Kline and French laboratories discloses 1-(n-methylsulfinyl)-1-(n-methylthio)-2-nitroethene as an intermediate in the preparation of histamine $H_2$-antagonisis. The patent does not disclose or suggest the compound as having antimicrobial activity.

Antimicrobially active compounds used in this invention may be prepared by known alkylation and oxidation methods. For example, a stirred solution of the potassium salt of 1,1-dimercapto-2-nitroethene ("PS") in solution with a solvent mixture such as methanol and water or chloroform and water can be reacted with an appropriately substituted alkylating agent to yield 1,1-bis(alkylthio)-2-nitroethene as product. The alkylation reaction occurs at room temperature within 2–48 hours. The product is then oxidized by a variety of procedures known in the literature to yield the corresponding sulfinyl or sulfonyl derivatives, such as by dissolving it in glacial acetic acid, stirring at 60°–70° C., and adding hydrogen peroxide, or by treatment with m-chloroperbenzoic acid. Typically, the oxidation reaction is complete within 14 hours.

Suitable alkylating agents useful in this invention include $(C_1-C_{18})$alkyl halides, and $(C_2-C_{18})$alkyl dihalides.

The antimicrobially active compounds used in this invention are typically obtained as a mixture of E and Z isomers. The isomers may be separated from the mixture by any of a variety of known methods, such as column chromatography, high pressure liquid chromatography, recrystallization and the like. The compounds of the invention are effective as antimicrobial agents as the mixture of E and Z isomers, the pure E isomer, or the pure Z isomer.

Suitable antimicrobially active compounds for use in this invention include for example:

1. 1-(Methylsulfinyl)-1-(methylthio)-2-nitroethene
2. 1-(Ethylsulfinyl)-1-(ethylthio)-2-nitroethene
3. 1-(n-Butylsulfinyl)-1-(n-butylthio)-2-nitroethene
4. 1-(n-Hexylsulfinyl)-1-(n-hexylthio)-2-nitroethene
5. 1-(n-Octylsulfinyl)-1-(n-octylthio)-2-nitroethene
6. 1-(n-Decylsulfinyl)-1-(n-decylthio)-2-nitroethene
7. 1-(n-Dodecylsulfinyl)-1-(n-dodecylthio)-2-nitroethene
8. 1-(n-Benzylsulfinyl)-1-(n-benzylthio)-2-nitroethene
9. 1,1-Bis(methylsulfinyl)-2-nitroethene
10. 2-(1itromethylene)-1-oxide-1,3-dithiolane
11. 2-(Nitromethylene)-1-oxide-1,3-dithiane
12. 1-Nitro-2-(methylsulfinyl)cyclopentene
13. 1-Nitro-2-(methylsulfinyl)cyclohexene
14. 1-Nitro-2-(methylsulfonyl)cyclopentene
15. 1-Nitro-2-(methylsulfonyl)cyclohexene
16. 1-Nitro-2-(phenylsulfinyl)cyclopentene
17. 1-Nitro-2-(phenylsulfinyl)cyclohexene
18. 1-Nitro-2-(phenylsulfonyl)cyclopentene
19. 1-Nitro-2-(phenylsulfonyl)cyclohexene
20. 5-Nitro-3,4-dihydro-2H-1-oxide-thiopyran
21. 2-Nitromethylene-1,3-benzodithiol-1-S-oxide
22. 2-Nitromethylene-6-methyl-1,3-benzodithiol-1-S-oxide
23. 2-Ethylsulfinyl-1-nitrobutene The use of antimicrobially active compound 1 is preferred.

The antimicrobially active compounds used in this invention can be used to inhibit the growth of microbial organisms by introducing an antimicrobially effective amount of one or more of said compounds onto, into, or at a locus subject to microbial attack. Loci such as wood, paint, adhesive, caulk, mastic, latex, pulp and paper slurries, textile, leather, plastics, cardboard, lubricants, cosmetics, detergents, household products, industrial cooling water, metal working fluid, pigment slurries, photographic processing fluids, and fuels can be protected.

The amount of antimicrobially active compound suitable to inhibit the growth of microbial organisms is from about 5 to 300 ppm based on the weight of said locus. Generally, the antimicrobially active compound is applied in a carrier such as water, solvent, or the like.

It is known in the art that the performance of antimicrobially active compounds may be enhanced by combination with one or more other antimicrobially active compounds. Thus, other known antimicrobially active compounds may be combined advantageously with the antimicrobially active compounds of this invention.

EXAMPLE 1

Preparation of 1,1-Bis(alkylthio)-2-nitroethenes 1,1-Bis(alkylthio)-2-nitro-ethenes were prepared according to one of the two general methods described below.

General Method A. To a stirred solution of 160 ml of methanol, 240 ml of water, and 0.16 mol of PS, 0.32 mol of alkyl halide was added dropwise. The mixture was stirred for several hours after which the reaction mixture was filtered and the solid material was washed with water and then ethanol to yield the 1,1-bis(alkylthio)-2-nitroethene compounds.

General Method B. To a stirred solution of 150 ml of chloroform, 150 ml of water, and 0.10 mol of PS, 0.2 mol of alkyl halide was added dropwise. After the addition of the alkyl halide was completed, 0.05 mol of tetrabutylammonium bromide was added. The solution was stirred for up to two days at room temperature, then the organic layer was seperated. The aqueous layer was extracted with chloroform. The organic solutions were combined and washed with water, then dried over anhydrous sodium sulfate. The solution was filtered and the solvent was removed under reduced pressure then the products were chromatographed on a silica gel column and eluted with a 1:10 ethyl acetate-petroleum ether solution to yield the 1,1-bis(alkylthio)-2-nitroethene compounds.

EXAMPLE 2

Oxidation of 1,1-Bis(alkylthio)-2-nitroethenes

The 1,1-bis(alkylthio)-2-nitroethene compounds, prepared above, were oxidized and isolated according to one of the following two methods:

General Method C. To a stirred solution of 10 mmol of 1,1-bis(alkylthio)-2-nitroethene in 45 ml glacial acetic acid, 10 mmol of hydrogen peroxide was added dropwise. The mixture was stirred at 60°–65° C. for 12 hours, then the solvent was removed under reduced pressure.

General Method D. Compounds were prepared according to method C. After the solvent was removed under reduced pressure, the solution was chromatographed on a silica gel column and eluted with a 1:7 ethyl acetate-petroleum ether solution.

EXAMPLE 3

Preparation of 1,1-Bis-(n-butylthio)-2-nitroethene 1,1-Bis-(n-butylthio)-2-nitroethene was prepared according to General Method B from n-butyl iodide and PS as the starting materials. The product was obtained in 97% yield as a brown-red oil and identified. $^1$H-NMR (CDCl$_3$): δ 7.10 (s, 1H), 3.03 (t, 3H), 2.94 (t, 3H), 1.40–1.80 (m, 8H), 0.95 (t, 3H), 0.93 ppm (t, 3H). Anal. calcd. for $C_{10}H_{19}NO_2S_2$: C, 48.16; H, 7.68; N, 5.61. Found C, 48.17; H, 6.95; N, 5.62.

EXAMPLE 4

Preparation of E and Z Isomers of 1-(n-Butylsulfinyl)-1-(n-butylthio)-2-nitroethene A mixture of E and Z isomers of 1-(n-butylsulfinyl)-1-(n-butylthio)-2-nitroethene was prepared from 1,1-bis-(n-butylthio)-2-nitroethene according to General Method D. The products were obtained as oils in 20% yield (isomer 1) and 45% yield (isomer 2) and identified. Isomer 1: $^1$H-NMR (CDCl$_3$): δ 7.66 (s, 1H), 3.02–3.23 (m, 2H), 2.73–2.93 (m, 2H), 1.65–1.95 (m, 4H), 1.40–1.60 (m, 4H), 0.98 (t, 3H), 0.96 ppm (t, 3H). Anal. calcd. for $C_{10}H_{19}NO_3S_2$: C, 45.52; H, 7.91; N, 5.27. Found C, 45.19; H, 7.27; N, 4.95. Isomer 2: $^1$H-NMR (CDCl$_3$): δ 6.93 (s, 1H), 2.73–3.25 (m, 4H), 1.43–2.05 (m, 8H), 0.97 (t, 3H), 0.96 ppm (t, 3H). Anal. Found C, 45.50; H, 7.41; N, 5.26

EXAMPLE 5

Preparation of 1,1-Bis-(n-dodecylthio)-2-nitroethene 1,1-Bis-(n-dodecylthio)-2-nitroethene was prepared according to General Method B from n-dodecyl iodide and PS as the starting materials. The product was obtained in 78% yield as a pale yellow solid and identified. $^1$H-NMR (CDCl$_3$): δ 7.08 (s, 1H), 3.04 (t, 2H), 2.94 (t, 2H), 1.20–1.80 (m, 40H), 0.85 ppm (t, 6H). Anal. calcd. for $C_{26}H_{51}NO_2S_2$: C, 65.91; H, 10.85; N, 2.96. Found C, 65.72; H, 11.35; N, 2.81.

EXAMPLE 6

Preparation of E and Z Isomers of 1-(n-Dodecylsulfinyl)-1-(n-dodecylthio)-2-nitroethene A mixture of E and Z isomers of 1-(n-Dodecylsulfinyl)-1-(n-dodecylthio)-2-nitroethene was prepared from 1,1-bis-(n-dodecylthio)-2-nitroethene according to General Method D. The mixture was obtained as a solid in 54% yield and identified. Anal. calcd. for $C_{26}H_{51}NO_3S_2$: C, 63.75; H, 10.50; N. 2.86. Found C, 63.78; H, 9.51; N, 3.07.

EXAMPLE 7

Preparation of 2-(nitromethylene)-1,3-dithiolane 2-(Nitromethylene)-1,3-dithiolane was prepared according to General Method B from 1,2-dibromoethane and PS as the starting materials. The product was obtained in 90% yield as yellow crystals and identified. $^1$H-NMR (CDCl$_3$): δ 7.57 (s, 1H), 3.54 ppm (s, 4H)

EXAMPLE 8

Preparation of E and Z Isomers of 2-(nitromethylene)-1-oxide-1,3-dithiolane

A mixture of E and Z isomers of 2-(nitromethylene)-1-oxide-1,3-dithiolane was prepared from 2-(nitromethylene)-1,3-dithiolane according to General Method D. The mixture was obtained as a solid in 37% yield and identified. Isomer 1: $^1$H-NMR (CDCl$_3$): δ 7.85 (s, 1H), 3.95–4.21 (m, 1H), 3.54–3.78 (m, 2H), 3.04–3.21 ppm (m, 1H).

EXAMPLE 9

Preparation of 2-(nitromethylene)-1,3-dithiane 2-(Nitromethylene)-1,3-dithiane was prepared according to General Method A from trimethylene dibromide and PS as the starting materials. The product was obtained in 82% yield as a solid and identified. Anal. calcd. for $C_5H_7NO_2S_2$: C, 33.88; H, 3.98; N, 7.90. Found C, 33.12; H, 3.75; N, 7.58.

EXAMPLE 10

Preparation of E and Z Isomers of 2-(nitromethylene)-1-oxide-1,3-dithiane

A mixture of E and Z isomers of 2-(nitromethylene)-1-oxide-1,3-dithiane was prepared from 2-(nitromethylene)-1,3-dithiane according to General Method C. The mixture was obtained in 37% yield as a solid and identified. Anal. calcd. for $C_5H_7NO_3S_2$: C, 31.08; H, 3.65; N, 7.25. Found C, 30.94; H, 3.49; N, 7.07.

EXAMPLE 11

Preparation of 2-Ethylsulfinyl-1-nitrobutene

4-Nitro-3-butanol was prepared according to the procedure for preparation of nitroalcohols as taught in *Organic Synthesis*, Volume 70, page 68, 1991.

2-Acetoxy-1-nitrobutane was prepared according to the procedure as taught in *Organic Synthesis*, Volume 70, page 68, 1991.

2-Ethylthio-1-nitrobutane was prepared by dropwise addition of a solution of triethylamine (16.77 g., 0.166 mol) and acetonitrile (50 ml.) to a stirred solution of 2-acetoxy-1-nitrobutane (26.50 g., 0.164 mol) and ethanethiol (11.20 g., 0.164 mol) over 30 minutes at 0°–5° C. Upon complete addition, the resulting solution was stirred for 1 hour at 0°–5° C., and then was poured into dilute aqueous hydrochloric acid solution (500 ml.). The organics were extracted into methylene chloride (3×150 ml.) and the combined portions were washed with deionized water (2×200 ml.), dried over magnesium sulfate, filtered and concentrated under reduced pressure. The product was distilled (1.5 Torr., 72°–75° C., internal) yielding a clear oil, 23.03 g., 86% yield. $^1$H-NMR (CDCl$_3$): δ 1.1, t, 3H, —CH$_3$; 1.29, t, 3H, SCH$_2$CH$_3$; 2.5–2.85, m, 2H, —CH$_2$—; 2.6, q, 2H, SCH$_2$—; 3.28, m, 1H, CH; 4.5, d, 2H, —CH$_2$NO$_2$.

2-Ethylthio-1-nitrobutene was prepared by adding a solution of sulfuryl chloride (20.16 g., 0.149 mol) in methylene chloride (30 ml.) to a stirred solution of 2-ethylthio-1-nitrobutane (23.02 g., 0.141 mol) in methylene chloride (100 ml.) at 0° C. The resulting solution was stirred for 15 minutes after addition was complete, and the volatile components were removed under reduced pressure. The residue was dissolved in methylene chloride (100 ml.) and a solution of triethylamine (14.27 g., 0.141 mol) in methylene chloride (30 ml.) was added at 0C. Once addition was complete, the solution was stirred for 15 minutes, and then was poured into dilute aqueous hydrochloric acid solution (400 ml.). The organics were separated and washed with deionized water (2×75 ml.), dried over magnesium sulfate, filtered and concentrated. Purification by silica gel chromatography (10:1 hexanes/ethyl acetate) yielded the product as a yellow oil, 2.85 g., 13% yield. $^1$H-NMR (CDCl$_3$): δ 1.26, m, 3H, —CH$_3$; 1.36, m, 3H, —CH$_3$; 2.55, q, 2H, —CH$_2$—; 2.92, q, 2H, SCH$_2$—; 7.2, s, 1H, olefinic H.

2-Ethylsulfinyl-1-nitrobutene was prepared by the dropwise addition of aqueous hydrogen peroxide (1.05 g., 0.0093 mol) to a stirred solution of 2-ethylthio-1-nitrobutene (1.50 g., 0.0093 mol) in formic acid (20 ml.). The resulting solution was stirred at room temperature for 18 hours. The solvent was removed under reduced pressure and the residue was dissolved in methylene chloride, washed successively with saturated aqueous sodium bicarbonate (1×50 ml.) and deionized water (1×50 ml.), dried over anhydrous magnesium sulfate, filtered and concentrated. Purification by silica gel chromatography (2:1 hexanes/ethyl acetate) afforded the isomeric mixture of the product as a yellow oil, 0.42g., 25% yield. $^1$H-NMR (CDCl$_3$): δ 1.26, m, 3H, CH$_3$; 1.5, t, 3H, CH$_3$; 2.5–2.85, m, 2H, —CH$_2$—; 2.85–3.2, m, 2H, SCH$_2$—; 7.2+7.3, 2s, 1H, olefinic H.

EXAMPLE 12

Physical Data

Melting points of some of the compounds of the invention were determined to be as follows:

TABLE 1

Melting Points

| Compound | Compound Name | Melting Point (°C.) |
|---|---|---|
| 1. | 1-(n-Methylsulfinyl)-1-(n-methylthio)-2-nitroethene | oil |
| 2. | 1-(n-Ethylsulfinyl)-1-(n-ethylthio)-2-nitroethene | oil |
| 3. | 1-(n-Butylsulfinyl)-1-(n-butylthio)-2-nitroethene | oil |
| 4. | 1-(n-Hexylsulfinyl)-1-(n-hexylthio)-2-nitroethene | oil |
| 5. | 1-(n-octylsulfinyl)-1-(n-octylthio)-2-nitroethene | semi-solid |
| 6. | 1-(n-Decylsulfinyl)-1-(n-decylthio)-2-nitroethene | 38–41 |
| 7. | 1-(n-Dodecylsulfinyl)-1-(n-dodecylthio)-2-nitroethene | 45–48 |
| 8. | 1-(n-Benzylsulfinyl)-1-(n-benzylthio)-2-nitroethene | 110–112 |
| 9. | 1,1-Bis(methylsulfinyl)-2-nitroethene | 106–108 |
| 10. | 2-(Nitromethylene)-1-oxide-1,3-dithiolane | 86–88 |
| 11. | 2-(Nitromethylene)-1-oxide-1,3-dithiane | 88–90 |

EXAMPLE 13

Antimicrobial Agent Test

The spectrum of antimicrobial activity and the effect of anionic surfactant on the antimicrobial activity of the antimicrobially active compounds of this patent are determined in Minimum Inhibitory Concentration(MIC) tests. MICs are determined by two fold serial dilutions of a compound in Minimal Salts Media(M9G), Tryptocase Soy Broth(TSB) or Trytocase Soy Broth and anionic surfactant(TSBA). The compounds are tested against *Aspergillus niger, Rhodoturola rubra, Escherichia coli* and *Pseudomonas aeruginosa*.

TABLE 2

Minimum Inhibitory Concentration (ppm)

| Compound | E. Coli M9G | E. Coli TSB | P. aeruginosa TSB | A. niger TSB | R. Rubra TSB | E. coli TSBA |
|---|---|---|---|---|---|---|
| 1 | <4 | 125 | 125 | 12.5 | 25 | 125 |
| 2 | 63 | >500 | >500 | >50 | >50 | 500 |
| 3 | 63 | 500 | >500 | 6.3 | 6.3 | 500 |
| 4 | >500 | >500 | >500 | 12.5 | 50 | >500 |
| 5 | >500 | >500 | >500 | >50 | >50 | >500 |
| 6 | >500 | >500 | >500 | >50 | >50 | >500 |
| 7 | >500 | >500 | >500 | >50 | >50 | >500 |
| 9 | 125 | 250 | 125 | 25 | 50 | 125 |
| 10 | 63 | 500 | >500 | >50 | >50 | 500 |
| 11 | 63 | 250 | 250 | >50 | >50 | 125 |

What is claimed is:

1. A method of controlling or inhibiting the growth of microorganisms comprising introducing in, at, or on a locus an antimicrobially effective amount of an antimicrobially active compound of the formula

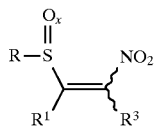 (I)

wherein
R¹ is selected from $R^2SO_y$, H, and $(C_1-C_{18})$alkyl;
R and R² are independently selected from $(C_1-C_{18})$alkyl;
R³ is selected from H, and $(C_1-C_6)$alkyl;
x=1 or 2; and
y=0, 1, or 2.

2. The method of claim 1 wherein said locus is selected from the group consisting of wood, paint, adhesive, caulk, mastic, latex, pulp or paper slurries, textile, leather, plastics, cardboard, lubricants, cosmetics, detergents, household products, industrial cooling water, metal working fluid, pigment slurries, photographic processing fluids, and fuels.

3. The method according to claim 1 wherein the amount of said antimicrobially active compound used to inhibit the growth of microbial organisms is from about 5 to 300 ppm based on the weight of said locus.

4. The method of claim 1 wherein said antimicrobially active compound is selected from the group consisting of: 1-(methylsulfinyl)-1-(methylthio)-2-nitroethene; 1-(ethylsulfinyl)-1-(ethylthio)-2-nitroethene; 1-(n-butylsulfinyl)-1-(n-butylthio)-2-nitroethene; 1-(n-hexylsulfinyl)-1-(n-hexylthio)-2-nitroethene; 1-(n-octylsulfinyl)-1-(n-octylthio)-2-nitroethene; 1-(n-decylsulfinyl)-1-(n-decylthio)-2-nitroethene; 1-(n-dodecylsulfinyl)-1-(n-dodecylthio)-2-nitroethene; 1,1-bis(methylsulfinyl)-2-nitroethene; 1-nitro-2-(methylsulfinyl)cyclopentene; 1-nitro-2-(methylsulfinyl)cyclohexene; 1-nitro-2-(methylsulfonyl)cyclopentene; 1-nitro-2-(methylsulfonyl)cyclohexene; 1-nitro-2-(phenylsulfinyl)cyclopentene; 1-nitro-2-(phenylsulfinyl)cyclohexene; 1-nitro-2-(phenylsulfonyl)cyclopentene; 1-nitro-2-phenylsulfonyl)cyclohexene; and 2-ethylsulfinyl-1-nitrobutene.

5. The method of claim 4 wherein said antimicrobially active compound is 1-(methylsulfinyl)-1-(methylthio)-2-nitroethene.

* * * * *